(12) United States Patent
Meffert et al.

(10) Patent No.: US 7,019,061 B2
(45) Date of Patent: Mar. 28, 2006

(54) POLYURETHANE AND THE USE THEREOF FOR MODIFYING RHEOLOGICAL PROPERTIES

(75) Inventors: Helmut Meffert, Ludwigshafen (DE); Son Nguyen Kim, Hemsbach (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 617 days.

(21) Appl. No.: 10/258,939

(22) PCT Filed: May 7, 2001

(86) PCT No.: PCT/EP01/05163

§ 371 (c)(1),
(2), (4) Date: Oct. 29, 2002

(87) PCT Pub. No.: WO01/85821

PCT Pub. Date: Nov. 15, 2001

(65) Prior Publication Data

US 2003/0113285 A1    Jun. 19, 2003

(30) Foreign Application Priority Data

May 8, 2000 (DE) ................... 10022247

(51) Int. Cl.
*C08G 18/48* (2006.01)
(52) U.S. Cl. ............ 524/284; 524/442; 524/875; 528/28; 528/49
(58) Field of Classification Search ............ None
See application file for complete search history.

(56) References Cited

U.S. PATENT DOCUMENTS

| | | | |
|---|---|---|---|
| 4,079,028 A | | 3/1978 | Emmons et al. |
| 5,281,654 A | | 1/1994 | Eisenhart et al. |
| 5,863,972 A | * | 1/1999 | Beckelmann et al. ....... 524/186 |
| 6,316,573 B1 | | 11/2001 | Klauck et al. |

FOREIGN PATENT DOCUMENTS

| | | |
|---|---|---|
| EP | 307 775 | 3/1989 |
| EP | 601 383 | 6/1994 |
| EP | 875 557 | 11/1998 |
| EP | 913 414 | 5/1999 |
| WO | 97/31046 | 8/1997 |
| WO | 97/36572 | 10/1997 |
| WO | 97/36573 | 10/1997 |
| WO | 98/17243 | 4/1998 |
| WO | 98/17705 | 4/1998 |

* cited by examiner

*Primary Examiner*—Rachel Gorr
(74) *Attorney, Agent, or Firm*—Novak Druce & Quigg LLP; Jason D. Voight

(57) ABSTRACT

A polyurethane which contains, as incorporated units,
  a) at least one diisocyanate,
  b) at least one polyether having two active hydrogen atoms per molecule and
  c) at least one compound of the formula I $$R^1\text{—}Z^1 \quad (I)$$

where
  $R^1$ is $C_8$- to $C_{30}$-alkyl, $C_8$- to $C_{30}$-alkenyl, aryl-$C_6$–$C_{22}$-alkyl or aryl-$C_6$–$C_{22}$-alkenyl, the alkyl group having 1, 2, 3 or 4 nonneighboring double bonds, and
  $Z^1$ is OH, SH or $NHR^2$, $R^2$ being hydrogen, $C_1$- to $C_6$-alkyl or $C_5$- to $C_8$-cycloalkyl,
and its use are described.

7 Claims, No Drawings

POLYURETHANE AND THE USE THEREOF FOR MODIFYING RHEOLOGICAL PROPERTIES

The present invention relates to a polyurethane, its use for modifying the rheological properties of homogeneous or heterogeneous compositions which contain at least one hydrophobic compound, and compositions which contain these polyurethanes.

For the preparation of cosmetic, pharmaceutical and industrial products, hydrophobic substances which are liquid at room temperature are frequently used. These liquids are, for example, aliphatic or cycloaliphatic hydrocarbons and hydrocarbon mixtures, oils, fats and other commercially available solvents which are only slightly soluble in water, if at all. Cosmetic, pharmaceutical, and industrial compositions frequently have to meet specific requirements with regard to their rheological properties. Often, they can be brought into the desired form for use only with the aid of additives, i.e. thickeners. Examples of conventional low molecular weight thickeners are the alkali metal and aluminum salts of fatty acids, fatty alcohols or waxes. However, the use of the known thickeners is frequently associated with disadvantages, depending on the field of use of the formulation to be thickened. Thus, either the thickening effect of the thickener may be unsatisfactory, its use may be undesired or its incorporation into the formulation to be thickened may be complicated or completely impossible, for example owing to its incompatibility with the water-insoluble compound to be thickened. A current demand which is made especially with regard to cosmetic and pharmaceutical compositions is to keep the content of nonactive substances, such as thickeners, very low.

It is known that the rheological properties of substantially water-insoluble liquids can be modified by using polymers. These have the advantage that, provided they are soluble in the hydrophobic substance, they generally make it possible to establish the viscosity as a function of their molecular weight.

A frequent disadvantage with the use of polymers as thickeners for the preparation of relatively high-viscosity or waxy or gel-like formulations is that, with increasing molecular weight of the polymer, its incorporation generally becomes more difficult, and that finally in many cases only swelling of the polymer instead of the desired dissolution is observable. Where solvents are used as assistants for the preparation of such formulations, they can often no longer be removed completely from the mixture.

WO-A-98/17243 and WO-A-98/17705 describe the use of ester-terminated polyamides for the formulation of transparent gels from liquid hydrocarbons having low polarity. The disadvantage of using these polyamides is that the resulting gels yellow in the course of time and various completely synthetic oils, such as silicone oils, cannot be thickened in this manner.

WO-A-97/36572 describes a base composition for the preparation of cosmetic compositions which contains at least one liquid silicone and at least one gel-forming composition. The gel formers used are polymers which contain siloxane groups and polar groups suitable for the formation of hydrogen bonds. The latter groups are selected from ester groups, urethane groups, urea groups, thiourea groups and amido groups. It is true that this document states very generally that the gel formers may also be terminally saturated, for example with $C_1$–$C_{20}$-monoalcohols. However, the use as gel formers of polyurethanes which contain, as incorporated units, at least one diisocyanate, at least one polyether and at least one compound having an active hydrogen atom and a long-chain alkyl or alkenyl group is not described. Moreover, the polymers described are still worthy of improvement with regard to their thickening effect. Thus, cosmetic formulations in stick form can be obtained only with the use of very large amounts of thickener, in the region of about 60%, based on the total formulation, or with the aid of additional emollients (waxes) e.g. $C_{12}$- to $C_{15}$-alkyl lactates. In the formulation of multiphase systems, it is essential to use surfactants. In addition, the polymers used as gel former are not suitable as thickeners for oils which are not based on silicone. Furthermore, the thickening of oil mixtures comprising silicone oils and further oils differing therefrom is not described in this publication.

WO-A-97/36573 describes a base composition for the preparation of cosmetic compositions which contains at least one liquid silicone and a gel former based on a combination of a wax and a polyamide. The wax and/or the polymer are modified with a siloxane group. The mixture used as a gel former is intended in particular for the preparation of formulations having a high silicone oil content. Thickening of mixtures of silicone oils and other oils or exclusively of oils not based on silicone is not described.

The unpublished German patent application P 199 41 365.7 describes oligomers containing urethane and/or urea groups and their use for modifying the rheological properties of hydrophobic liquids. The use as thickeners of polyurethanes which contain as incorporated units at least one compound having an active hydrogen atom and a relatively long-chain alkyl or alkenyl group is not described in the this document.

It is an object of the present invention to provide novel polyurethanes. These should preferably be suitable for modifying the rheological properties of homogeneous or heterogeneous compositions which contain at least one substantially water-insoluble liquid.

It is further an object of the present invention to provide a composition which contains at least one hydrophobic compound which is liquid at ambient temperature and whose rheological properties or consistency can be adjusted within a very wide range. It should be possible to use silicone-free liquids, silicones and mixtures thereof as the hydrophobic compounds. Preferably, the water-insoluble compound should be capable of being readily stirred into the formulation at >40° C. without a solvent. Preferably, the compositions should permit the preparation of cosmetic, pharmaceutical and industrial compositions whose rheological properties can be adjusted within a wide range from the liquid to the solid form.

We have found, surprisingly, that this object is achieved by a polyurethane which contains, as incorporated units, at least one diisocyanate, at least one polyether having two groups reactive to isocyanate groups and at least one compound having a group reactive to isocyanate groups and a hydrocarbon radical having at least eight carbon atoms.

The present invention therefore relates to a polyurethane which contains, as incorporated units, a) at least one diisocyanate,
b) at least one polyether having two active hydrogen atoms per molecule and
c) at least one compound of the formula I $$R^1\text{—}Z^1 \qquad (I)$$

where $R^1$ is $C_8$- to $C_{30}$-alkyl, $C_8$- to $C_{30}$-alkenyl, aryl-$C_6$–$C_{22}$-alkyl or aryl-$C_6$–$C_{22}$-alkenyl, the alkenyl groups having 1, 2, 3 or 4 nonneighboring double bonds, and $Z^1$ is OH, SH or $NHR^2$, where $R^2$ is hydrogen, $C_1$- to $C_6$-alkyl or $C_5$- to $C_8$-cycloalkyl.

Preferably, the polyurethane additionally contains, as incorporated units, at least one component which is selected from d) polysiloxanes having at least two active hydrogen atoms per molecule, e) compounds which differ from a) to d), have a molecular weight of from 56 to 600 and contain two active hydrogen atoms per molecule and mixtures thereof.

In the context of the present invention, the expression polyurethanes also includes polymers which have urea groups and/or thiourea groups instead of or in addition to the urethane groups.

The polyurethanes preferably have from 2 to 50, in particular from 3 to 45, urethane and/or urea groups per molecule.

Preferred polyurethanes are those which have a molecular weight of from about 500 to 10 000, preferably from 700 to 9 000, in particular from 1 000 to 8 000.

The polyurethanes preferably have no free isocyanate groups.

The diisocyanates a) are preferably selected from aliphatic, cycloaliphatic and/or aromatic diisocyanates, such as tetramethylene diisocyanate, hexamethylene diisocyanate, methylene diphenyl diisocyanate, tolylene 2,4- and 2,6-diisocyanate and their isomer mixtures, o-, m- and p-xylylene diisocyanate, naphthylene 1,5-diisocyanate, cyclohexylene 1,4-diisocyanate, dicyclohexylmethane diisocyanate and mixtures thereof, in particular isophorone diisocyanate, hexamethylene diisocyanate and/or dicyclohexylmethane diisocyanate. Hexamethylene diisocyanate is particularly preferably used. If desired, up to 3 mol % of said compounds may be replaced by triisocyanates.

The component b) is preferably a polyetherdiol having a number average molecular weight of from about 250 to 7 000, preferably from about 300 to 6 000 g/mol. Preferred polyetherdiols are polyalkylene glycols, e.g. polyethylene glycols, polypropylene glycols, polytetrahydrofurans, copolymers of ethylene oxide, propylene oxide and/or butylene oxide which contain the alkylene oxide units polymerized in random form or in the form of blocks, etc.

Preferably used components b) are polytetrahydrofurans and mixtures which contain them.

Suitable polytetrahydrofurans (polytetramethylene glycols) b) can be prepared, for example, by cationic polymerization of tetrahydrofuran in the presence of acidic catalysts, e.g. sulfuric acid or fluorosulfuric acid. Such preparation processes are known to a person skilled in the art. The number-average molecular weight of the poly(THF) component b) is preferably from about 250 to 6 000 g/mol, particularly preferably from 500 to 5 000 g/mol, in particular from 650 to 4 000 g/mol.

Suitable components b) are furthermore polyaryl ethers, e.g. polyphenylene oxide, polyxylenols and their alkoxylates. Suitable polyxylenols (poly(oxy-2,6-dimethyl-p-phenylene)s) can be prepared, for example, by oxidative polymerization of 2,6-dimethylphenol in the presence of copper/amine complexes. Suitable poly(oxy-2,6-diphenyl-p-phenylene)s can be prepared, for example, by oxidative coupling of m-terphenyl-2'-ol. Such preparation processes are known to a person skilled in the art.

Suitable components b) are furthermore polyether ketones, e.g. polyaryl ether ketones, these preferably being compounds having phenylene radicals linked via ether and keto groups. The preparation of suitable polyaryl ether ketones is carried out, for example, by polycondensation of 4-phenoxybenzoyl chloride or of terephthaloyl dichloride and diphenyl ether in the presence of Friedel-Crafts catalysts, e.g. $AlCl_3$.

The total amount of the polyaryl ethers and/or polyether ketones is preferably not more than 20, in particular not more than 10, % by weight, based on the total amount of the component b).

The component c) preferably comprises at least one compound of the formula I, where $R^1$ is a straight-chain or branched $C_8$- to $C_{30}$-alkyl or $C_8$- to $C_{30}$-alkenyl radical, it being possible for the alkenyl radical to have 1, 2, 3 or 4 nonneighboring double bonds. They are preferably straight-chain or branched $C_{12}$- to $C_{28}$-alkyl or alkenyl radicals, particularly preferably $C_{16}$- to $C_{26}$-alkyl or alkenyl radicals. They are preferably predominantly linear alkyl and/or alkenyl radicals that also occur in natural or synthetic fatty acids and fatty alcohols and oxo alcohols.

$R^1$ in the formula I is preferably n-octyl, ethylhexyl, 1,1,3,3-tetramethylbutyl, n-nonyl, n-decyl, n-undecyl, n-dodecyl, n-tridecyl, myristyl, pentadecyl, palmityl (=cetyl), heptadecyl, octadecyl (=stearyl), nonadecyl, arachinyl, behenyl, lignocerenyl, cerotinyl, melissinyl, etc. Particularly preferable radicals $R^1$ are heptadecyl and stearyl.

The compound of the formula I is preferably at least one primary alcohol or thioalcohol or a primary amine, where $R^1$ is $C_8$- to $C_{30}$-alkyl or alkenyl. The compound of the formula I is then preferably 1-octyl, 1-nonyl, 1-decyl, 1-undecyl, 1-undec-10-enyl, 1-tridecyl, 1-tetradecyl, 1-pentadecyl, 1-hexadecyl, 1-heptadecyl, 1-octadecyl, 1-octadeca-9,12-dienyl, 1-nonadecyl, 1-eicosyl, 1-eicos-9-enyl, 1-heneicosyl or 1-docosyl alcohol, thiol and/or amine. The compound of the formula I is particularly preferably stearyl alcohol and/or stearylamine.

The polysiloxanes d) are preferably a compound of the formula II $$E^1-(CH_2)_i-\left[\begin{array}{c}R^4\\|\\Si-O\\|\\R^5\end{array}\right]_k\begin{array}{c}R^4\\|\\Si-(CH_2)_l-E^2\\|\\R^5\end{array} \quad (II)$$

where $R^4$ and $R^5$, independently of one another, are each $C_1$- to $C_4$-alkyl, benzyl or phenyl, $E^1$ and $E^2$, independently of one another, are each OH or $NHR^6$, where $R^6$ is hydrogen, $C_1$- to $C_6$-alkyl or $C_5$- to $C_8$-cycloalkyl, i and l, independently of one another, are each from 2 to 8 and k is from 3 to 50, and mixtures thereof.

Suitable alkyl radicals are, for example, methyl, ethyl, n-propyl, isopropyl, n-butyl, tert-butyl, n-pentyl, n-hexyl, etc. Suitable cycloalkyl radicals are, for example, cyclopentyl, cyclohexyl, cycloheptyl, cyclooctyl, etc.

$R^4$ and $R^5$ are preferably both methyl.

These polysiloxanes d) preferably have a number-average molecular weight of from about 300 to 5 000, preferably from 400 to 3 000.

The component e) is preferably selected from compounds of formula III

$$X-R^7-Y \qquad (III)$$

where

X and Y, independently of one another, are each OH or $NHR^8$, where $R^8$ is hydrogen, $C_8$- to $C_{30}$-alkyl or $C_8$- to $C_{30}$-alkenyl, it being possible for the alkenyl radical to have 1, 2, 3 or 4 nonneighboring double bonds, and $R^7$ is a divalent bridging group having 2 to 25 atoms in the chain between the flanking bonds.

$R^7$ is preferably a $C_2$- to $C_{10}$-alkylene bridge which may have one, two or three nonneighboring double bonds and/or one, two or three substituents which are selected from alkyl, alkoxy, hydroxyl, cycloalkyl and aryl, it being possible for the alkylene bridge additionally to be interrupted by one, two or three nonneighboring, unsubstituted or substituted heteroatoms and/or for the alkylene bridge to be singly, doubly or triply fused to aryl.

Component e) preferably comprises diols, diamines, amino alcohols and mixtures thereof. The molecular weight of these compounds is preferably from about 56 to 500. If desired, up to 3 mol % of said compounds may be replaced by triols or triamines.

Diols are preferably used as component e). Suitable diols are, for example, ethylene glycol, propylene glycol, butylene glycol, neopentyl glycol, dimethylolcyclohexane, di-, tri-, tetra-, penta- or hexaethylene glycol and mixtures thereof. Hexaethylene glycol, neopentyl glycol and/or dimethylolcyclohexane are preferably used.

Preferred components e) are furthermore compounds of the formula $X-(CH_2)_{1-4}-O-(p-C_6H_4)-CH_2-(p-C_6H_4)-O-(CH_2)_{1-4}-Y$, where X and Y, independently of one another, are each OH or $NHR^9$, where $R^9$ is hydrogen, $C_1$- to $C_8$-alkyl or $C_5$- to $C_8$-cycloalkyl.

Particularly preferred component e) is 2,2-bis(4-(hydroxyethoxy)phenyl)methane, which is commercially available under the name Dianol®22 (from Akzo Nobel).

Suitable amino alcohols e) are, for example, 2-aminoethanol, 2-(N-methylamino)ethanol, 3-aminopropanol, 4-aminobutanol, 1-ethylaminobutan-2-ol, 2-amino-2-methyl-1-propanol, 4-methyl-4-aminopentan-2-ol, etc.

Suitable diamines e) are, for example, ethylenediamine, propylenediamine, 1,4-diaminobutane, 1,5-diaminopentane and 1,6-diaminohexane.

Preferred diamines e) are diamines of the formula $R^a-NH-(CH_2)_{2-3}-NH_2$, where $R^a$ is $C_{10}$- to $C_{30}$-alkyl or $C_{10}$- to $C_{30}$-alkenyl, it being possible for the alkenyl radical to have 1, 2 or 3 nonneighboring double bonds. The molecular weight of these diamines e) is preferably from about 160 to 400.

Other suitable diamines e) are, for example, hexamethylenediamine, piperazine, 1,2-diaminocyclohexane, 1,3-diaminocyclohexane, 1,4-diaminocyclohexane, neopentanediamine, 4,4'-diaminodicyclohexylmethane, etc.

The novel polyurethanes are prepared, for example, by reacting at least one diisocyanate a) with those groups of components b), c) and, if required, d) and/or e) which are reactive toward isocyanate groups. Preferably, the reaction is carried out at elevated temperatures of from about 60 to 140° C., in particular from about 70 to 100° C. The reaction can be carried out in the melt without a solvent or in a suitable solvent or solvent mixture. Suitable solvents are, for example, aprotic polar solvents, such as tetrahydrofuran, ethyl acetate, N-methylpyrrolidone, dimethylformamide and preferably ketones, such as acetone and methyl ethyl ketone.

If the novel polyurethanes are used as a component of a composition which has at least one hydrophobic liquid compound (oil or fat component), the preparation of the polyurethanes is preferably carried out in this oil component as a solvent. The reaction is preferably effected under an inert gas atmosphere, e.g. under nitrogen. The components are preferably used in amounts such that the ratio of the number of NCO equivalents of the compounds of component a) to the number of equivalents of active hydrogen atoms of the components b), c) and, if required, d) and/or e) is from about 0.9:1 to 1.1:1.

The present invention furthermore relates to the use of at least one polyurethane, as defined above, as a component of a homogeneous or heterogeneous composition which contains at least one water-insoluble compound liquid at 20° C. for modifying the rheological properties of this composition.

The present invention furthermore relates to a process for modifying the rheological properties of a homogeneous or heterogeneous composition which contains at least one water-insoluble compound liquid at 20° C., the composition being mixed with at least one polyurethane as defined above and, if required, heated.

Modifying rheological properties is understood widely in the context of the present invention. The novel polyurethanes are suitable in general for thickening the consistency of hydrophobic compounds in a wide range. Depending on the starting consistency of the hydrophobic liquid compound (s), as a rule flow properties from low-viscosity to solid (no longer flowing) can be achieved depending on the amount of the polyurethane used. Modifying rheological properties is therefore understood as meaning, inter alia, the increase in the viscosity of liquids, the improvement of the thixotropic properties of gels, the solidification of gels and waxes, etc.

Regardless of their number of components, homogeneous compositions have only a single phase. Heterogeneous compositions are disperse systems of two or more components immiscible with one another. These preferably include emulsions, e.g. O/W and W/O formulations which have at least one of the oil or fat components described above and water as immiscible phases. The novel polyurethanes are generally used in the oil phase.

Suitable water-insoluble compounds which are liquid at 20° C. and whose rheological properties can be modified by the novel polyurethanes are referred to below as component B).

The present invention furthermore relates to a composition containing

A) at least one polyurethane, as defined above, and
B) at least one water-insoluble compound liquid at 20° C.

Preferably, the novel compositions contain at least one polyurethane A) which contains, as polymerized units, from 10 to 30, preferably from 12 to 25, % by weight of at least one diisocyanate a), from 30 to 80, preferably from 35 to 70, % by weight of at least one polyether b), from 9 to 30, preferably from 7 to 25, % by weight of at least one component c), from 0 to 40, preferably from 0.01 to 35, in particular from 0.1 to 25, % by weight of at least one polysiloxane d) and from 0 to 20, preferably from 1 to 18, in particular from 3 to 15, % by weight of at least one component e).

According to a preferred embodiment, the novel compositions contain polyurethanes containing siloxane groups. According to a further preferred embodiment, the novel compositions contain at least one siloxane-free polyurethane. For polyurethanes containing siloxane groups, the weight ratio of polyether b) to polysiloxane component d) is preferably from about 99.9:0.1 to 50:50, preferably from 99:1 to 60:40, in particular from 95:5 to 80:20.

The siloxane-free polyurethanes used according to the invention preferably contain, as component b), at least one polytetrahydrofuran. If desired, up to about 50, preferably about 30, % by weight of this may be replaced by at least one polyether b) differing from polytetrahydrofuran.

The novel compositions comprise at least one substantially water-insoluble (hydrophobic) liquid B) (oil or fat component). Water-insoluble is understood as meaning a water solubility of, as a rule, not more than 1 g/l at 20° C.

The novel compositions preferably comprise at least one component B) which is selected from oils, preferably mineral oils, fully synthetic oils, oils of vegetable and animal origin and essential oils,
fats,
saturated acyclic and cyclic hydrocarbons,
esters of monocarboxylic acids with monohydric, dihydric or trihydric alcohols,
silicone oils and mixtures thereof.

The novel composition comprise, for example, an oil or fat component B) which is selected from hydrocarbons of low polarity, such as mineral oils; linear saturated hydrocarbons, such as tetradecane, hexadecane, octadecane, etc.; cyclic hydrocarbons, such as decahydronaphthalene; branched hydrocarbons; esters, preferably esters of fatty acids, e.g. the esters of $C_1$- to $C_{24}$-monoalcohols with $C_1$- to $C_{22}$-monocarboxylic acids, such as isopropyl isostearate, n-propyl myristate, iso-propyl myristate, n-propyl palmitate, iso-propyl palmitate, hexacosanyl palmitate, octacosanyl palmitate, triacontanyl palmitate, dotriacontanyl palmitate, tetratriacontanyl palmitate, hexacosanyl stearate, octacosanyl stearate, triacontanyl stearate, dotriacontanyl stearate, tetratriacontanyl stearate; salicylates, such as $C_1$- to $C_{10}$-salicylates, e.g. octyl salicylate; benzoate esters, such as $C_{10}$- to $C_{15}$-alkyl benzoates, benzyl benzoate; other cosmetic esters, such as fatty acid triglycerides, propylene glycol monolaurate, polyethylene glycol monolaurate, castor oil, $C_{10}$- to $C_{15}$-alkyl lactates, etc.

Suitable silicone oils B) are, for example, linear polydimethylsiloxanes, poly(methylphenylsiloxanes), cyclic siloxanes and mixtures thereof. The number-average molecular weight of the polydimethylsiloxanes and poly(methylphenylsiloxanes) is preferably from about 1000 to 150 000 g/mol. Preferred cyclic siloxanes have 4- to 8-membered rings. Suitable cyclic siloxanes are commercially available, for example, under the name cyclomethicone.

The novel oil-containing or fat-containing compositions contain said component B) in general in an amount of from about 1 to 99.9, preferably from 10 to 90, in particular from 20 to 80, % by weight, based on the total weight of the composition.

The novel compositions and oil- or fat-containing products based thereon can in general be adjusted within a wide range with regard to their rheological properties or their consistency. The novel compositions are thus preferably suitable for formulating oil- or fat-containing cosmetic, pharmaceutical and industrial products. Depending on the starting consistency of the component B) and any additional components used for formulating products, the properties can generally be varied from a low-viscosity to a solid consistency depending on the amount of polyurethane A) used. Preferably, the solutions of the polyurethanes A) in the component B) are in general clear. Advantageously, formulations, in particular cosmetic formulations, can thus be colored without impairment by the natural color of the novel composition.

According to a preferred embodiment, the novel compositions contain at least one polyurethane A), which contains at least one polysiloxane d) as incorporated units, and a component B) which comprises at least one silicone oil.

According to a further preferred embodiment either the polyurethane A) or the component B) is silicone-free. In particular, both the polyurethane A) and the component B) are silicone-free. Polyurethanes A) which contain as incorporated units a polyether component b) which comprises at least one polytetrahydrofuran are preferably used for thickening silicone-free components B). Surprisingly, the novel compositions which comprise silicone-free components A) and/or B) nevertheless have good performance characteristics. For example, the rheological properties of these composition can as a rule be adjusted in an advantageous manner.

The present invention furthermore relates to the use of compositions, as defined above, as or in cosmetic and pharmaceutical formulation(s), as or in coating and treatment compositions for nonabsorptive surfaces, preferably metals, plastics, textile man-made fibers and glass, and for absorptive surfaces, preferably wood, paper, cotton and leather.

The present invention furthermore relates to the use of compositions, as defined above, for the preparation of candles, combustion and power fuels, industrial greases, antirust compositions and ink jet printer cartridges.

The present invention furthermore relates to the use of polyurethanes A), as described above, as components of pharmaceutical, cosmetic and industrial formulations, preferably in cosmetic formulations for the treatment of skin, and for modifying the rheological properties of compositions based on compounds of low polarity.

The present invention furthermore relates to a cosmetic or pharmaceutical composition, containing at least one polyurethane, as defined above,
at least one water-insoluble compound liquid at 20° C.,
at least one cosmetically or pharmaceutically active substance and
if required, at least one additive.

According to a preferred embodiment, the novel cosmetic compositions are present in the form of an oil-containing or fat-containing cosmetic preparation. These include, for example, creams, mascara, eye make-up, face make-up, cosmetic oils, baby oil, bath oil, make-up removers, skin moisturizers, sunscreen agents, lipcare compositions, anhydrous hand wash compositions, medical ointments, etc.

The novel oil-containing or fat-containing cosmetic compositions contain the component B) in general in an amount of from about 1 to 99.9, preferably from 10 to 90, in particular from 20 to 80, % by weight, based on the total weight of the composition.

The novel oil-containing or fat-containing cosmetic compositions contain the polyurethanes A) described above in general in an amount of from about 0.1 to 50, preferably from 0.2 to 30, in particular from 0.5 to 10, % by weight, based on the total amount of the composition.

Furthermore, the oil-containing or fat-containing cosmetic compositions may contain assistants and/or additives, such as emulsifiers, superfatting agents, stabilizers, waxes, consistency regulators, thickeners, silicone compounds, biogenic active ingredients, film formers, preservatives, hydrotropic agents, solubilizers, UV absorbers, colorants and fragrances, etc.

The oil- or fat-containing cosmetic products based on the polyurethanes described above can in general be adjusted within a wide range with regard to their rheological properties or their consistency. Depending on the starting consistency of the cosmetic composition, the properties can generally be varied from a low-viscosity to a solid consistency depending on the amount of the oligomer used. Advantageously, cosmetic skin products which have a high proportion of low-viscosity oil- or fat-containing components can thus be formulated.

The polyurethanes described and the novel compositions based on them are advantageously suitable for formulating gels. Gel is understood in general as meaning a formulation which has a higher viscosity than a liquid and which is self-supporting, i.e. retains a shape imparted to it, without a shape-stabilizing envelope. All abovementioned oil components which are liquid at ambient temperature are generally suitable for formulating gels. Advantageously, gels based on the polyurethanes described above are generally transparent. They can be formulated with conventional additives to give novel cosmetic compositions, e.g. lipcare compositions, deodorants, antiperspirants, make-ups, etc. The polyurethanes described and the novel compositions based on them can also advantageously be used for the preparation of noncosmetic gel-based products. These include, for example, automotive waxes and polishes, candles, furniture polishes, metal cleaners, household cleaners, etc.

The novel polyurethanes and the novel compositions based on them are advantageously also suitable for the preparation of conventional O/W and W/O formulations, e.g. creams, the polyurethanes generally being used in the oil phase.

The novel polyurethanes are particularly suitable as thickeners for liquids of low polarity, preferably oils. Preferably used as thickeners for oils are polyurethanes which contain not more than 5% by weight, based on the total weight, of urethane and/or urea groups. These components are preferably highly compatible with non-silicone-containing oils. They are generally soluble in silicone oils, non-silicone-containing oils or mixtures thereof. Advantageously, the solutions obtained are generally clear. Advantageously, clear cosmetic formulations can, for example, be more easily colored than already colored ones. The novel polyurethanes and the novel compositions based on them are preferably suitable for use in personal care products, for example cosmetic compositions, e.g. eye make-up, face make-up, baby oil, bath oil, make-up removers, skin moisturizers, sunscreen agents, lipcare compositions, anhydrous hand wash compositions, medical ointments, perfumes and suppositories. They are furthermore advantageously suitable for formulating cosmetic hair products, such as hair sprays, foam setting compositions, hair mousse, hair gel and shampoos. They are furthermore preferably suitable for use in beauty cosmetics, in particular in mascara and eyeshadow. Furthermore, the polyurethanes described above and their reaction products can advantageously be used in household products, such as automotive waxes and polishes, candles, furniture polishes, metal cleaners and metal polishes, household cleaners, paint removers and carriers for insecticides.

They are furthermore suitable for use in technical or industrial products, for example in fuels, greases, soldering pastes, antirust compositions and ink jet printer cartridges.

The nonrestrictive examples which follow illustrate the invention.

EXAMPLES

I. Polyurethane Preparation

Polyurethane 1:

58.38 g of polytetrahydrofuran ($M_n=1\,000$ g/mol), 6.19 g of diethylene glycol, 15.79 g of stearyl alcohol and 0.1 g of tetrabutyl orthotitanate were initially taken in a four-necked flasked equipped with a stirrer, a dropping funnel, a thermometer, a reflux condenser and an apparatus for working under nitrogen and, while stirring, the mixture was heated to about 70° C. and homogenized. 19.64 g of hexamethylene diisocyanate were then added dropwise while stirring, the reaction temperature increasing. The reaction mixture was further stirred at 80° C. until the NCO content was less than 0.01 mol % of the starting content (from about 4 to 5 hours).

Polyurethane 2:

Analogously to polyurethane 1, a polyurethane was prepared from 61.26 g of polytetrahydrofuran ($M_n=1\,000$ g/mol), 6.03 g of 1,6-hexanediol, 13.81 g of stearyl alcohol and 18.89 g of hexamethylene diisocyanate.

Polyurethane 3:

Analogously to the preparation method for the polyurethane 1, a polyurethane was prepared from 61.26 g of polytetrahydrofuran ($M_n=1\,000$ g/mol), 6.03 g of 1,6-hexanediol, 13.81 g of stearyl alcohol and 18.89 g of hexamethylene diisocyanate at about 80° C. in 30 ml of acetone as solvent.

Polyurethane 4:

Analogously to the preparation method for polyurethane 3, a polyurethane was prepared from 42.67 g of polytetrahydrofuran ($M_n=1\,000$ g/mol), 12.72 g of Duomeen® T from Ceca ($C_{12}$- to $C_{24}$-alkyl fatty diamine), 23.08 g of stearyl alcohol and 21.53 g of hexamethylene diisocyanate.

Polyurethane 5:

Analogously to the preparation method for polyurethane 3, a polyurethane was prepared from 42.34 g of polytetrahydrofuran ($M_n=1\,000$ g/mol), 13.38 g of 2,2-bis(4-(hydroxyethoxy)phenyl)methane (Dianol® 22 from Akzo Nobel), 22.91 g of stearyl alcohol and 21.37 g of hexamethylene diisocyanate in methyl ethyl ketone as solvent.

For the preparation of formulations of the abovementioned polyurethanes, these were mixed with the oil component according to Table 1 and heated to a temperature of from 50 to 180° C. until the polyurethane had completely gone into solution. After cooling, a mixture having modified rheological properties was obtained. The properties of the mixture are likewise shown in Table 1.

Performance Characteristics

TABLE 1

| Polyurethane from example | Oil | Polyurethane concentration [% by weight] | Appearance of the cooled composition |
|---|---|---|---|
| 1 | Finsolv ® TN | 10 | solid, slightly turbid |
| 2 | Finsolv ® TN | 10 | solid, opaque |
| 3 | Liquid paraffin | 10 | solid, opaque to slightly turbid |
| 3 | Finsolv ® TN | 10 | solid, opaque |
| 3 | Finsolv ® TN | 20 | solid, opaque |
| 3 | Finsolv ® TN/Silicone oil 80/20 | 20 | solid, opaque to slightly turbid |
| 4 | Finsolv ® TN | 10 | viscous, slightly turbid |
| 5 | Finsolv ® TN | 10 | viscous, slightly turbid |

Finsolv ® TN = $C_{12}$- to $C_{15}$-alkyl benzoate

We claim:

1. A composition comprising at least one polyurethane which contains, as incorporated units,
   a) at least one diisocyanate,
   b) at least one polytetrahydrofuran having two active hydrogen atoms per molecule and
   c) at least one compound of the formula I $$R^1\!-\!Z^1 \qquad (I)$$

where
   $R^1$ is $C_8$- to $C_{30}$-alkyl, $C_8$- to $C_{30}$-alkenyl, aryl-$C_6$–$C_{22}$-alkyl or aryl-$C_6$–$C_{22}$-alkenyl, the alkenyl groups having 1, 2, 3 or 4 nonneighboring double bonds, and
   $Z^1$ is OH, SH or $NHR^2$, where $R^2$ is hydrogen, $C_1$- to $C_6$-alkyl or $C_5$- to $C_8$-cycloalkyl
   and additionally at least one component which is selected from
   d) polysiloxanes having at least two active hydrogen atoms per molecule,
   e) compounds which differ from a) to d), have a molecular weight of from 56 to 600 and contain two active hydrogen atoms per molecule and mixtures thereof,
      as a component of a homogeneous or heterogeneous composition which contains at least one water-soluble compound liquid at 20° C. for modifying the rheological properties of this composition.

2. A process for modifying the rheological properties of a homogeneous or heterogeneous composition which contains at least one water-insoluble compound liquid at 20° C., the composition being mixed with at least one polyurethane, as defined in claim 1, and, if required, heated.

3. A composition containing
   A) at least one polyurethane, as defined in claim 1, and
   B) at least one water-insoluble compound liquid at 20° C.

4. A composition as claimed in claim 3, the component B) being selected from
   oils, preferably mineral oils, fully synthetic oils, oils of vegetable and animal origin and essential oils,
   fats,
   saturated acyclic and cyclic hydrocarbons,
   esters of monocarboxylic acids with monohydric, dihydric or trihydric alcohols,
   silicone oils
   and mixtures thereof.

5. A composition, as defined in claim 3, as or in cosmetic and pharmaceutical formulation(s), as or in coating and treatment composition(s) for nonabsorptive surfaces, preferably metals, plastics, textile man-made fibers and glass, and for absorptive surfaces, preferably wood, paper, cotton and leather.

6. A composition, as defined in claim 3, for the preparation of candles, combustion and power fuels, industrial greases, antirust compositions and ink jet printer cartridges.

7. A cosmetic or pharmaceutical composition containing
   at least one polyurethane, as defined in claim 1,
   at least one water-insoluble compound liquid at 20° C.,
   at least one cosmetically or pharmaceutically active substance and
   if required, at least one additive.

* * * * *